(12) United States Patent
Nogami et al.

(10) Patent No.: US 9,885,732 B2
(45) Date of Patent: Feb. 6, 2018

(54) ANALYSIS DEVICE AND ANALYSIS METHOD

(71) Applicant: Hitachi High-Technologies Corporation, Minato-ku, Tokyo (JP)

(72) Inventors: Makoto Nogami, Tokyo (JP); Shinya Ito, Tokyo (JP); Tadao Yabuhara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 41 days.

(21) Appl. No.: 14/911,406

(22) PCT Filed: Jun. 24, 2014

(86) PCT No.: PCT/JP2014/066623
§ 371 (c)(1),
(2) Date: Feb. 10, 2016

(87) PCT Pub. No.: WO2015/025610
PCT Pub. Date: Feb. 26, 2015

(65) Prior Publication Data
US 2016/0195561 A1    Jul. 7, 2016

(30) Foreign Application Priority Data
Aug. 23, 2013 (JP) .................. 2013-173154

(51) Int. Cl.
*G01N 35/02* (2006.01)
*G01N 33/543* (2006.01)
(Continued)

(52) U.S. Cl.
CPC ..... *G01N 35/025* (2013.01); *G01N 33/54366* (2013.01); *G01N 35/00871* (2013.01);
(Continued)

(58) Field of Classification Search
CPC ............... G01N 33/54366; G01N 35/1065
See application file for complete search history.

(56) References Cited

U.S. PATENT DOCUMENTS

2004/0265173 A1    12/2004   Matsumoto et al.
2011/0157580 A1     6/2011   Nogami et al.
(Continued)

FOREIGN PATENT DOCUMENTS

JP        6-74967 U      10/1994
JP     2004-333259 A     11/2004
(Continued)

OTHER PUBLICATIONS

International Search Report (PCT/ISA/210) issued in PCT Application No. PCT/JP2014/066623 dated Sep. 16, 2014, with English translation (five (5) pages).
(Continued)

Primary Examiner — P. Kathryn Wright
(74) Attorney, Agent, or Firm — Crowell & Moring LLP

(57) ABSTRACT

An analysis device is provided with a first disk on which a sample container and disposable container can be disposed, a second disk on which a solid-phase extraction cartridge and disposable container can be disposed, a first probe capable of transferring a sample of the sample container disposed on the first disk or a solution of the disposable container disposed on the first disk to the solid-phase extraction cartridge or disposable container disposed on the second disk, and a second probe capable of transferring a reagent of a reagent container to the sample container or disposable container disposed on the first disk and the solid-phase extraction cartridge or disposable container disposed on the second disk. Sample preprocessing before solid-phase extraction processing takes place on the first disk.

4 Claims, 17 Drawing Sheets

(51) Int. Cl.
*G01N 35/10* (2006.01)
*G01N 35/00* (2006.01)
G01N 1/28 (2006.01)
G01N 35/04 (2006.01)

(52) U.S. Cl.
CPC . *G01N 35/1065* (2013.01); *G01N 2001/2826* (2013.01); *G01N 2035/0458* (2013.01)

(56) References Cited

U.S. PATENT DOCUMENTS

| | | |
|---|---|---|
| 2012/0039748 A1 | 2/2012 | Mimura et al. |
| 2012/0206713 A1 | 8/2012 | Nogami et al. |
| 2012/0322139 A1 | 12/2012 | Nogami et al. |

FOREIGN PATENT DOCUMENTS

| | | |
|---|---|---|
| JP | 2006-7081 A | 1/2006 |
| JP | 2010-101726 A | 5/2010 |
| JP | 2010-217057 A | 9/2010 |
| JP | 2011-85503 A | 4/2011 |
| JP | 2011-95069 A | 5/2011 |
| JP | 2012-251937 A | 12/2012 |
| JP | 2013-96733 A | 5/2013 |
| WO | WO 2010-026837 A1 | 3/2010 |
| WO | WO 2011/108177 A1 | 9/2011 |

OTHER PUBLICATIONS

Japanese-language Written Opinion (PCT/ISA/237) issued in PCT Application No. PCT/JP2014/066623 dated Sep. 16, 2014 (four (4) pages).

[FIG. 1]
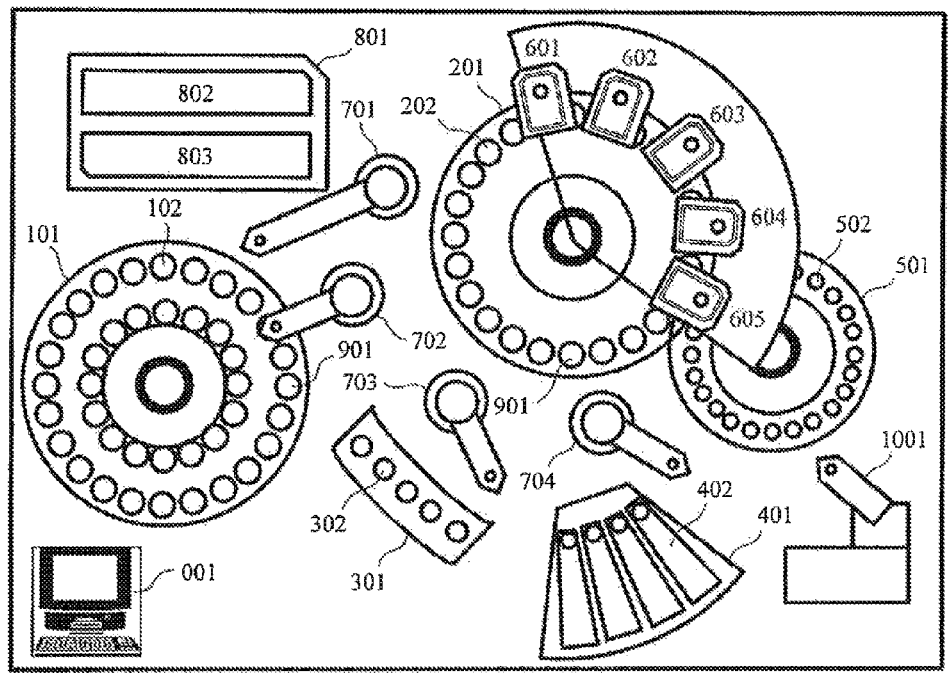
[FIG. 2A]
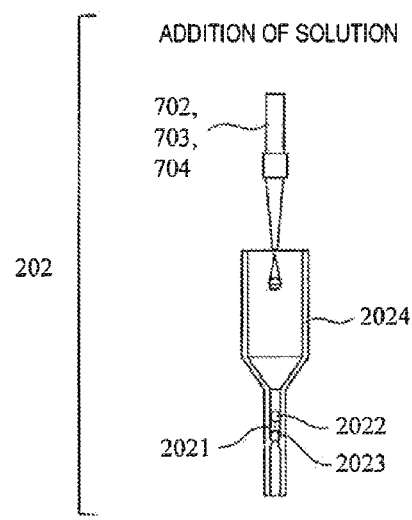

[FIG. 2B]
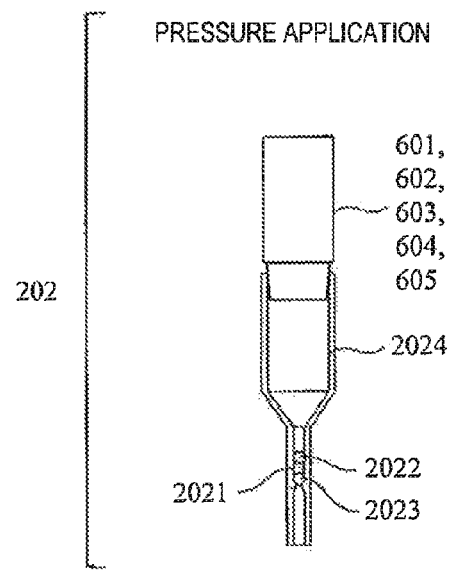
[FIG. 3]
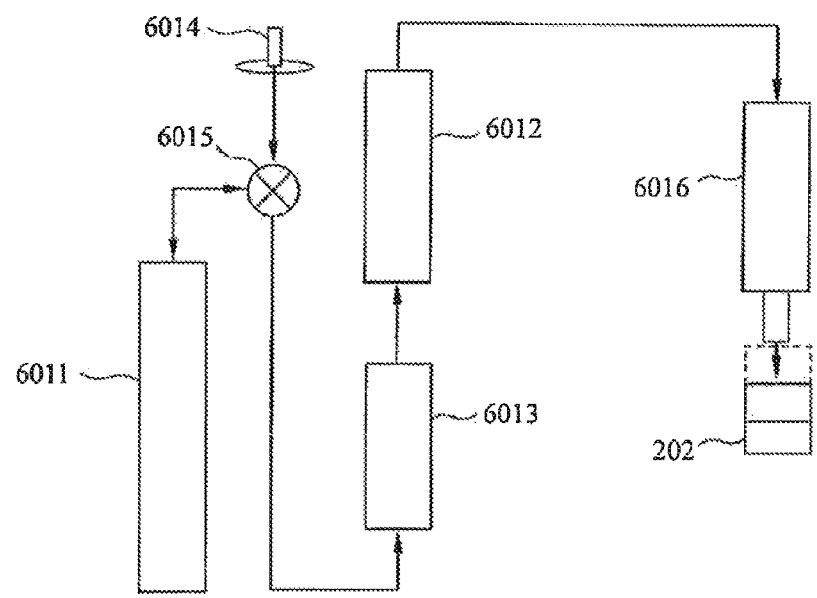

[FIG. 4]
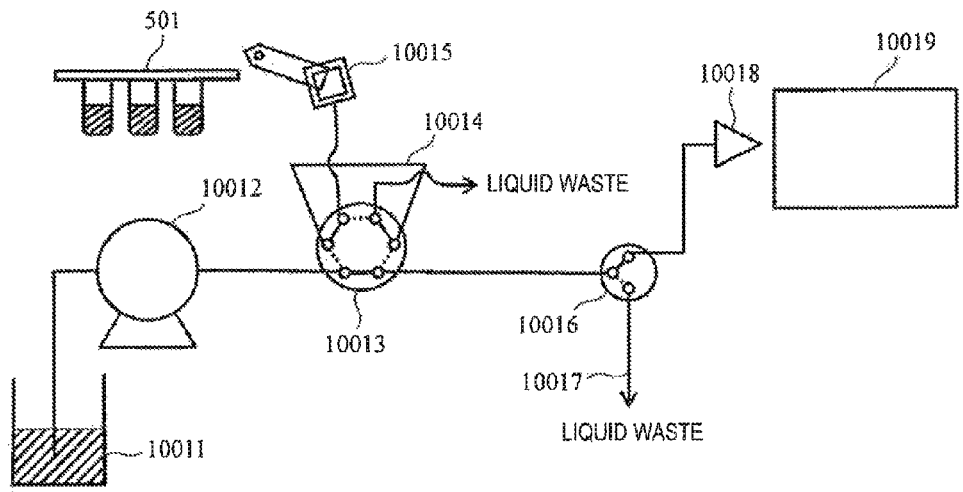
[FIG. 5]
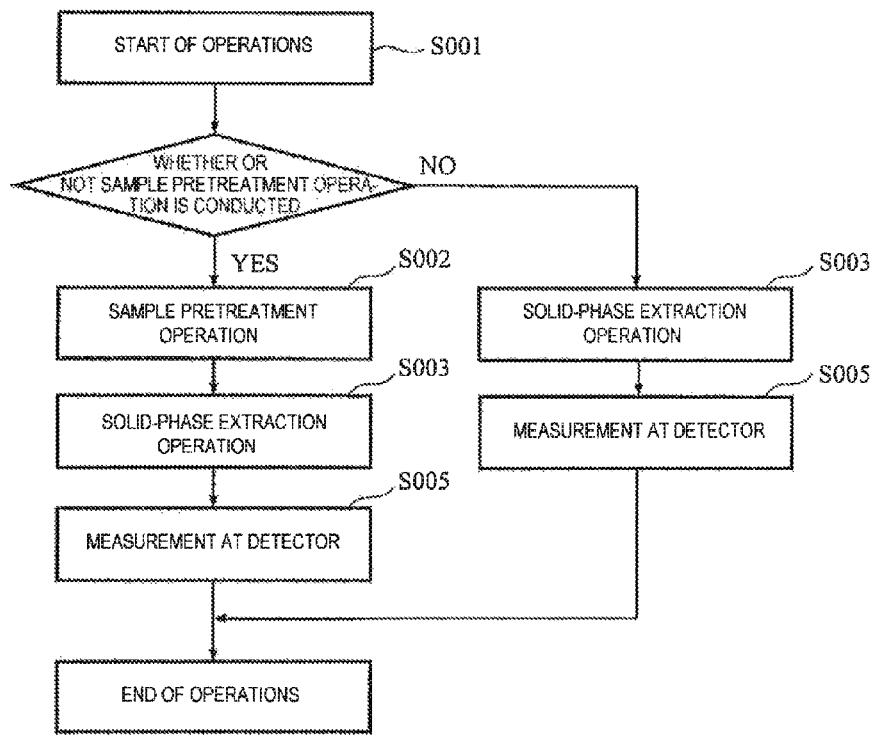

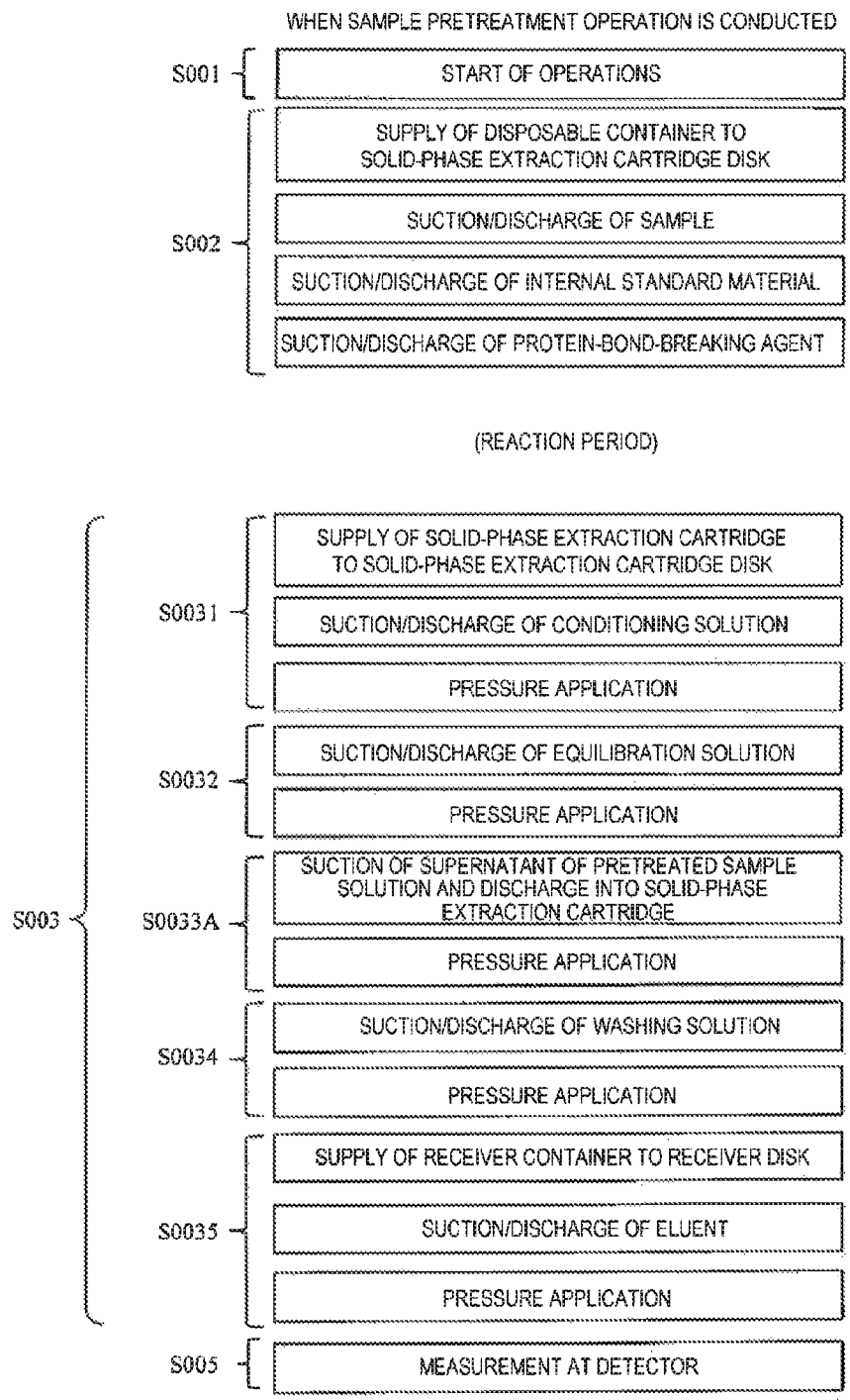
[FIG. 6A]

[FIG. 6B]
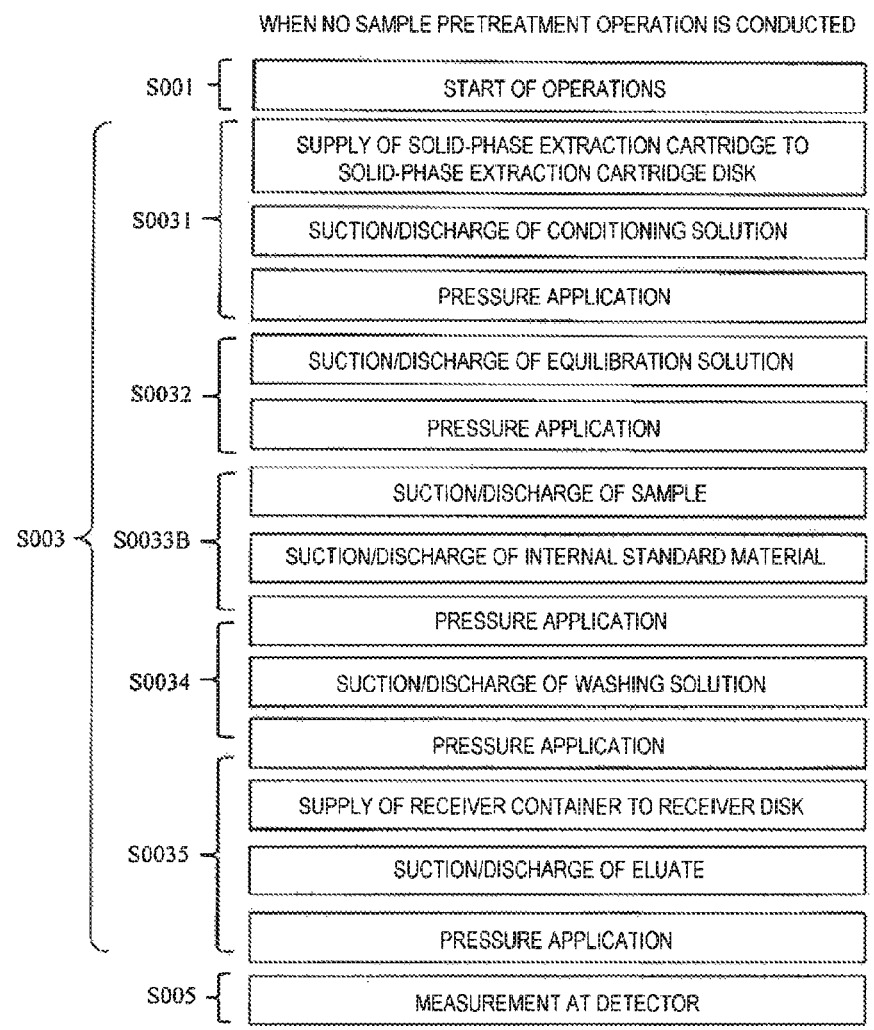

[FIG. 7A]

| TIME (MINUTE) | SAMPLE 1 WITH SAMPLE PRETREATMENT OPERATION | SAMPLE 2 WITHOUT SAMPLE PRETREATMENT OPERATION |
|---|---|---|
| 1 | S001,S002 | |
| 2 | | |
| 3 | | |
| 4 | | |
| 5 | | |
| 6 | | |
| 7 | | S001,S0031 |
| 8 | | S0032 |
| 9 | | S0033B |
| 10 | | S0034 |
| 11 | | S0035 |
| 12 | | |
| 13 | | |
| 14 | | |
| 15 | | |
| 16 | | |
| 17 | | |
| 18 | | |
| 19 | | |
| 20 | | |
| 21 | S0031 | |
| 22 | S0032 | |
| 23 | S0033A | |
| 24 | S0034 | |
| 25 | S0035 | |
| 26 | | |
| 27 | | |
| 28 | | |
| 29 | | |
| 30 | | |

[FIG. 7B]

| TIME (MINUTE) | SAMPLE 3 WITH SAMPLE PRETREATMENT OPERATION | SAMPLE 4 WITH SAMPLE PRETREATMENT OPERATION |
|---|---|---|
| 1 | | |
| 2 | | |
| 3 | S001,S002 | |
| 4 | | S001,S002 |
| 5 | | |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |
| 21 | | |
| 22 | | |
| 23 | S0031 | |
| 24 | S0032 | S0031 |
| 25 | S0033A | S0032 |
| 26 | S0034 | S0033A |
| 27 | S0035 | S0034 |
| 28 | | S0035 |
| 29 | | |
| 30 | | |

[FIG. 7C]

| TIME (MINUTE) | SAMPLE 5<br>WITHOUT SAMPLE PRETREATMENT OPERATION | SAMPLE 6<br>WITHOUT SAMPLE PRETREATMENT OPERATION |
|---|---|---|
| 1 | | |
| 2 | | |
| 3 | | |
| 4 | | |
| 5 | | |
| 6 | | |
| 7 | | |
| 8 | S001, S0031 | |
| 9 | S0032 | S001, S0031 |
| 10 | S0033B | S0032 |
| 11 | S0034 | S0033B |
| 12 | S0035 | S0034 |
| 13 | | S0035 |
| 14 | | |
| 15 | | |
| 16 | | |
| 17 | | |
| 18 | | |
| 19 | | |
| 20 | | |
| 21 | | |
| 22 | | |
| 23 | | |
| 24 | | |
| 25 | | |
| 26 | | |
| 27 | | |
| 28 | | |
| 29 | | |
| 30 | | |

[FIG. 7D]

| TIME (MINUTE) | SAMPLE 7 WITH SAMPLE PRETREATMENT OPERATION | SAMPLE 8 WITH SAMPLE PRETREATMENT OPERATION |
|---|---|---|
| 1 | | |
| 2 | | |
| 3 | | |
| 4 | S001,S002 | |
| 5 | | S001,S002 |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |
| 21 | | |
| 22 | | |
| 23 | | |
| 24 | S0031 | |
| 25 | S0032 | S0031 |
| 26 | S0033A | S0032 |
| 27 | S0034 | S0033A |
| 28 | S0035 | S0034 |
| 29 | | S0035 |
| 30 | | |

[FIG. 7E]

| TIME (MINUTE) | SAMPLE 9 WITH SAMPLE PRETREATMENT OPERATION | SAMPLE 10 WITHOUT SAMPLE PRETREATMENT OPERATION |
|---|---|---|
| 1 | | |
| 2 | | |
| 3 | | |
| 4 | | |
| 5 | | |
| 6 | S001, S002 | |
| 7 | | |
| 8 | | |
| 9 | | |
| 10 | | S001, S0031 |
| 11 | | S0032 |
| 12 | | S0033B |
| 13 | | S0034 |
| 14 | | S0035 |
| 15 | | |
| 16 | | |
| 17 | | |
| 18 | | |
| 19 | | |
| 20 | | |
| 21 | | |
| 22 | | |
| 23 | | |
| 24 | | |
| 25 | | |
| 26 | S0031 | |
| 27 | S0032 | |
| 28 | S0033A | |
| 29 | S0034 | |
| 30 | S0035 | |

[FIG. 8]
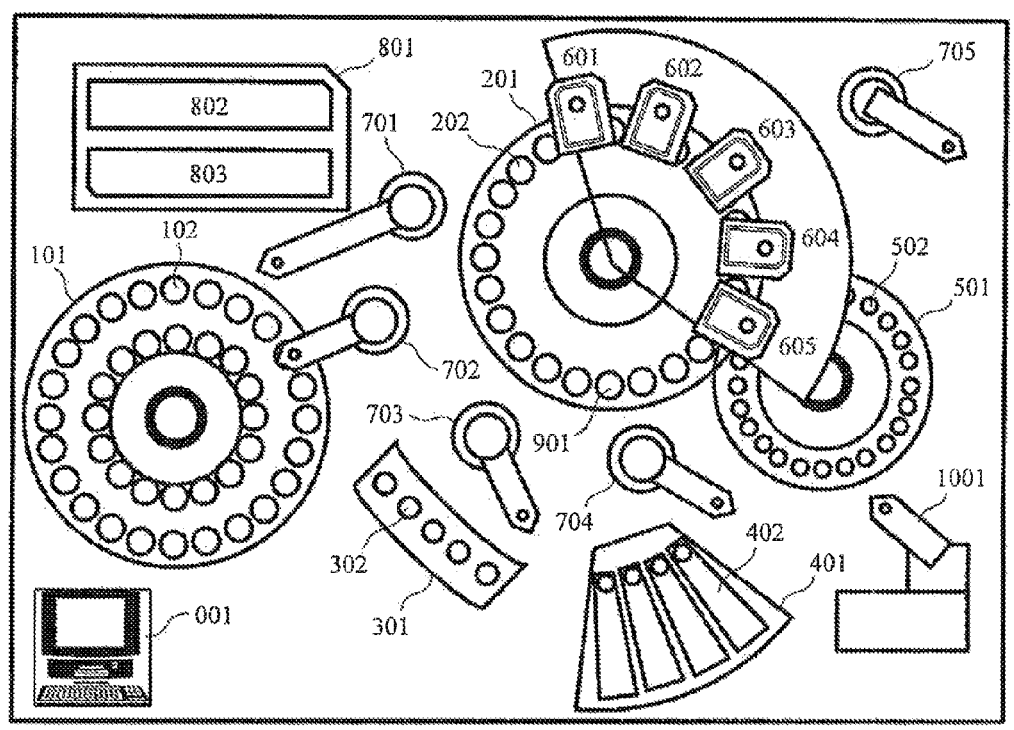

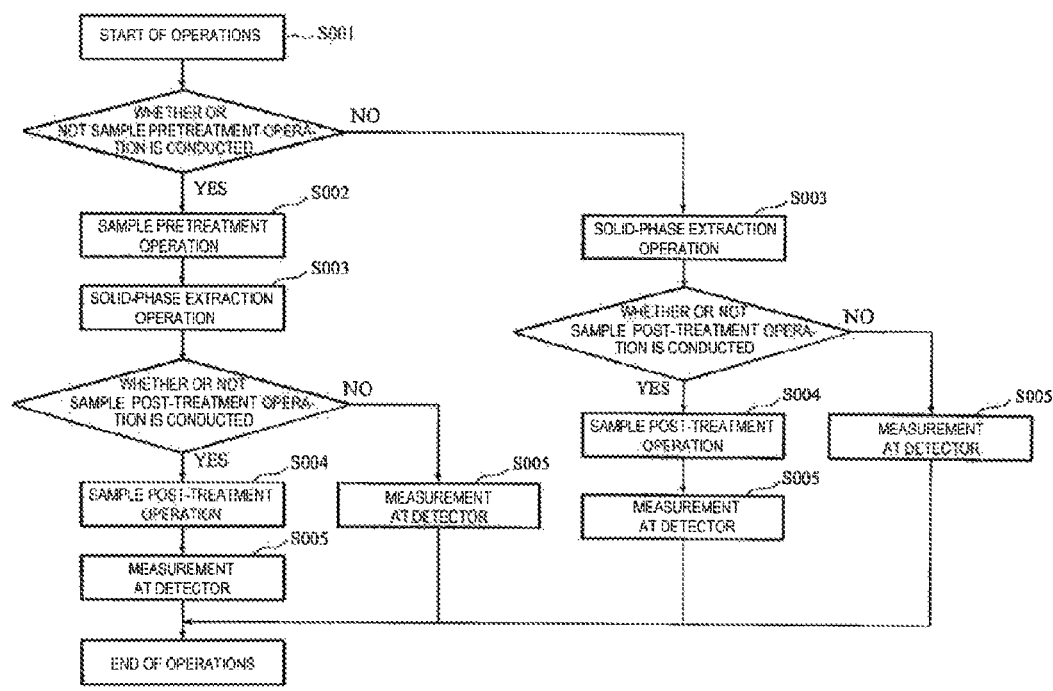
[FIG. 9]

[FIG. 10A]

| TIME (MINUTE) | SAMPLE 1 — WITH SAMPLE PRETREATMENT OPERATION WITH SAMPLE POST-TREATMENT OPERATION | SAMPLE 2 — WITHOUT SAMPLE PRETREATMENT OPERATION WITH SAMPLE POST-TREATMENT OPERATION |
|---|---|---|
| 1 | S001, S002 | |
| 2 | | |
| 3 | | |
| 4 | | |
| 5 | | |
| 6 | | |
| 7 | | |
| 8 | | |
| 9 | | S001, S003 |
| 10 | | |
| 11 | | |
| 12 | | S004 |
| 13 | | |
| 14 | | |
| 15 | | |
| 16 | | |
| 17 | | |
| 18 | | |
| 19 | | |
| 20 | | |
| 21 | | |
| 22 | | |
| 23 | S003 | |
| 24 | | |
| 25 | | |
| 26 | S004 | |
| 27 | | |
| 28 | | |
| 29 | | |
| 30 | | |

[FIG. 10B]

| TIME (MINUTE) | SAMPLE 3<br>WITH SAMPLE PRETREATMENT OPERATION<br>WITHOUT SAMPLE POST-TREATMENT OPERATION | SAMPLE 4<br>WITH SAMPLE PRETREATMENT OPERATION<br>WITH SAMPLE POST-TREATMENT OPERATION |
|---|---|---|
| 1 | | |
| 2 | | |
| 3 | S001,S002 | |
| 4 | | S001,S002 |
| 5 | | |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |
| 21 | | |
| 22 | | |
| 23 | | |
| 24 | S003 | |
| 25 | | S003 |
| 26 | | |
| 27 | | |
| 28 | | S004 |
| 29 | | |
| 30 | | |

[FIG. 10C]

| TIME (MINUTE) | SAMPLE 5 WITHOUT SAMPLE PRETREATMENT OPERATION WITH SAMPLE POST-TREATMENT OPERATION | SAMPLE 6 WITHOUT SAMPLE PRETREATMENT OPERATION WITH SAMPLE POST-TREATMENT OPERATION |
|---|---|---|
| 1 | | |
| 2 | | |
| 3 | | |
| 4 | | |
| 5 | | |
| 6 | | |
| 7 | | |
| 8 | | |
| 9 | | |
| 10 | S001, S003 | |
| 11 | | S001, S003 |
| 12 | | |
| 13 | S004 | |
| 14 | | S004 |
| 15 | | |
| 16 | | |
| 17 | | |
| 18 | | |
| 19 | | |
| 20 | | |
| 21 | | |
| 22 | | |
| 23 | | |
| 24 | | |
| 25 | | |
| 26 | | |
| 27 | | |
| 28 | | |
| 29 | | |
| 30 | | |

[FIG. 10D]

| TIME (MINUTE) | SAMPLE 7<br>WITH SAMPLE PRETREATMENT OPERATION<br>WITH SAMPLE POST-TREATMENT OPERATION | SAMPLE 8<br>WITH SAMPLE PRETREATMENT OPERATION<br>WITHOUT SAMPLE POST-TREATMENT OPERATION |
|---|---|---|
| 1 | | |
| 2 | | |
| 3 | | |
| 4 | S001, S002 | |
| 5 | | S001, S002 |
| 6 | | |
| 7 | | |
| 8 | | |
| 9 | | |
| 10 | | |
| 11 | | |
| 12 | | |
| 13 | | |
| 14 | | |
| 15 | | |
| 16 | | |
| 17 | | |
| 18 | | |
| 19 | | |
| 20 | | |
| 21 | | |
| 22 | | |
| 23 | | |
| 24 | | |
| 25 | | |
| 26 | S003 | |
| 27 | | S003 |
| 28 | | |
| 29 | S004 | |
| 30 | | |

[FIG. 10E]

| TIME (MINUTE) | SAMPLE 9<br>WITH SAMPLE PRETREATMENT OPERATION<br>WITHOUT SAMPLE POST-TREATMENT OPERATION | SAMPLE 10<br>WITHOUT SAMPLE PRETREATMENT OPERATION<br>WITH SAMPLE POST-TREATMENT OPERATION |
|---|---|---|
| 1 | | |
| 2 | | |
| 3 | | |
| 4 | | |
| 5 | | |
| 6 | S001, S002 | |
| 7 | | |
| 8 | | |
| 9 | | |
| 10 | | |
| 11 | | S001, S003 |
| 12 | | |
| 13 | | |
| 14 | | |
| 15 | | S004 |
| 16 | | |
| 17 | | |
| 18 | | |
| 19 | | |
| 20 | | |
| 21 | | |
| 22 | | |
| 23 | | |
| 24 | | |
| 25 | | |
| 26 | | |
| 27 | | |
| 28 | S003 | |
| 29 | | |
| 30 | | |

ANALYSIS DEVICE AND ANALYSIS METHOD

TECHNICAL FIELD

The present invention relates to an analyzer and an analysis method.

BACKGROUND ART

A background technique in this technical field is described in PTL 1. PTL 1 describes "an analyzer characterized by having a sample disk equipped with a sample container, a reagent disk equipped with a reagent container, a first disk equipped with a first container in which a component to be measured in the sample is purified, a second disk equipped with a second container in which the sample purified in the first container is purified and a mass spectrometer unit which measures the sample purified in the second container" (abstract).

CITATION LIST

Patent Literature

PTL 1: WO2011/108177

SUMMARY OF INVENTION

Technical Problem

PTL 1 describes an analyzer which can analyze an item with a low blood level highly accurately. In the analyzer of PTL 1, by conducting purification twice using the first disk and the second disk, an item with a low blood level can be analyzed highly accurately. However, because one kind of processing is conducted on one disk in the analyzer of PTL 1, the numbers of containers which can be installed on the respective disks should be increased, for example, to improve the throughput. As a result, the area of the entire apparatus sometimes becomes large. On the other hand, when the area of the entire apparatus is reduced, the numbers of containers which can be installed on the respective disks should be reduced, and the throughput sometimes decreases.

An object of the invention is to provide an analyzer capable of conducting different kinds of processing on a single disk.

Solution to Problem

In order to solve the problems, the structures described in the claims are employed for example. Although the present application includes a plurality of means for solving the problems, the following analyzer is provided for example. The analyzer has a first disk on which a sample container containing a sample and a disposable container can be placed, a second disk on which a solid-phase extraction cartridge for conducting solid-phase extraction and a disposable container can be placed, a third disk which is located under the solid-phase extraction cartridge and on which a receiver container for receiving an eluate after the solid-phase extraction can be placed, a reagent storage part in which a reagent container can be placed, a detector which measures a solid-phase extracted sample, a first probe capable of transferring the sample in the sample container or a solution in the disposable container placed on the first disk to the solid-phase extraction cartridge or the disposable container placed on the second disk, a second probe capable of transferring a reagent in the reagent container to the sample container or the disposable container placed on the first disk and to the solid-phase extraction cartridge or the disposable container placed on the second disk and a controller which controls the first disk, the second disk, the third disk, the detector, the first probe and the second probe. In the analyzer, sample pretreatment before the solid-phase extraction is conducted on the first disk.

According to another example, the following analysis method is provided. The analysis method uses an analyzer having a first disk on which a sample container containing a sample and a disposable container can be placed, a second disk on which a solid-phase extraction cartridge for conducting solid-phase extraction and a disposable container can be placed, a third disk which is located under the solid-phase extraction cartridge and on which a receiver container for receiving an eluate after the solid-phase extraction can be placed, a reagent storage part in which a reagent container can be placed, a detector which measures a solid-phase extracted sample, a first probe capable of transferring the sample in the sample container or a solution in the disposable container placed on the first disk to the solid-phase extraction cartridge or the disposable container placed on the second disk and a second probe capable of transferring a reagent in the reagent container to the sample container or the disposable container placed on the first disk and to the solid-phase extraction cartridge or the disposable container placed on the second disk. The analysis method includes a step of transferring the sample in the sample container placed on the first disk to the disposable container placed on the first disk or on the second disk using the first probe, a step of transferring the reagent in the reagent container to the disposable container placed on the first disk or on the second disk using the second probe, a step of conducting sample pretreatment before the solid-phase extraction on the first disk using the disposable container placed on the first disk or using the disposable container transferred from the second disk to the first disk, a step of transferring a solution after the sample pretreatment in the disposable container on the first disk to the solid-phase extraction cartridge on the second disk using the first probe, a step of conducting the solid-phase extraction in the solid-phase extraction cartridge on the second disk, a step of eluting the eluate after the solid-phase extraction into the receiver container on the third disk and a step of measuring the solid-phase extracted sample in the receiver container using the detector.

Advantageous Effects of Invention

According to the invention, different kinds of processing can be conducted on a single disk. Thus, the number of disks in the analyzer can be reduced while the throughput is maintained, and an analyzer with a small apparatus area can be provided.

Further characteristics related to the invention are disclosed by the present description and by the attached drawings. Also, problems, structures and effects other than those described above are disclosed by the explanations of Examples below.

BRIEF DESCRIPTION OF DRAWINGS

FIG. 1 A schematic plan view of an Example of the analyzer of the invention.

FIG. 2A A schematic view of the solid-phase extraction cartridge according to an Example of the analyzer of the invention.

FIG. 2B A schematic view of the solid-phase extraction cartridge according to an Example of the analyzer of the invention.

FIG. 3 A figure showing the structure of the pressure-applying unit according to an Example of the analyzer of the invention.

FIG. 4 A figure showing the structure of the detector according to an Example of the analyzer of the invention.

FIG. 5 A figure explaining the processing operations according to an Example of the analyzer of the invention.

FIG. 6A A figure explaining the processing operations according to an Example of the analyzer of the invention, where a sample pretreatment operation is conducted.

FIG. 6B A figure explaining the processing operations according to an Example of the analyzer of the invention, where no sample pretreatment operation is conducted.

FIG. 7A A figure explaining the scheduling of the processing operations according to an Example of the analyzer of the invention, where components to be measured which are subjected to a sample pretreatment operation and those which are not subjected to the sample pretreatment operation are mixed.

FIG. 7B A figure explaining the scheduling of the processing operations according to an Example of the analyzer of the invention, where components to be measured which are subjected to a sample pretreatment operation and those which are not subjected to the sample pretreatment operation are mixed.

FIG. 7C A figure explaining the scheduling of the processing operations according to an Example of the analyzer of the invention, where components to be measured which are subjected to a sample pretreatment operation and those which are not subjected to the sample pretreatment operation are mixed.

FIG. 7D A figure explaining the scheduling of the processing operations according to an Example of the analyzer of the invention, where components to be measured which are subjected to a sample pretreatment operation and those which are not subjected to the sample pretreatment operation are mixed.

FIG. 7E A figure explaining the scheduling of the processing operations according to an Example of the analyzer of the invention, where components to be measured which are subjected to a sample pretreatment operation and those which are not subjected to the sample pretreatment operation are mixed.

FIG. 8 A schematic plan view according to an Example of the analyzer of the second Example of the invention.

FIG. 9 A figure explaining the processing operations according to an Example of the analyzer of the second Example of the invention.

FIG. 10A A figure explaining the scheduling of the processing operations according to an Example of the analyzer of the invention, where components to be measured which are subjected to a sample pretreatment operation, those which are not subjected to the sample pretreatment operation, those which are subjected to a sample post-treatment operation and those which are not subjected to the sample post-treatment operation are mixed.

FIG. 10B A figure explaining the scheduling of the processing operations according to an Example of the analyzer of the invention, where components to be measured which are subjected to a sample pretreatment operation, those which are not subjected to the sample pretreatment operation, those which are subjected to a sample post-treatment operation and those which are not subjected to the sample post-treatment operation are mixed.

FIG. 10C A figure explaining the scheduling of the processing operations according to an Example of the analyzer of the invention, where components to be measured which are subjected to a sample pretreatment operation, those which are not subjected to the sample pretreatment operation, those which are subjected to a sample post-treatment operation and those which are not subjected to the sample post-treatment operation are mixed.

FIG. 10D A figure explaining the scheduling of the processing operations according to an Example of the analyzer of the invention, where components to be measured which are subjected to a sample pretreatment operation, those which are not subjected to the sample pretreatment operation, those which are subjected to a sample post-treatment operation and those which are not subjected to the sample post-treatment operation are mixed.

FIG. 10E A figure explaining the scheduling of the processing operations according to an Example of the analyzer of the invention, where components to be measured which are subjected to a sample pretreatment operation, those which are not subjected to the sample pretreatment operation, those which are subjected to a sample post-treatment operation and those which are not subjected to the sample post-treatment operation are mixed.

DESCRIPTION OF EMBODIMENTS

Examples of the invention are explained below by reference to the attached drawings. Although the attached drawings illustrate specific Examples according to the principles of the invention, the drawings are intended to promote understanding of the invention and should never be used to construe the invention narrowly. In all of the drawings for explaining the embodiments of the Examples, components having a same mechanism are given a same reference sign in principle, and a repetition of the same explanation is avoided as much as possible.

The analyzer of the invention can be applied to various analyzers such as an automated analyzer for medical substances, an automated immunoassay analyzer and an automated biochemical analyzer. The following Examples are explained using a disk-type mechanism as an example mechanism of transferring a sample and a solid-phase extraction cartridge. However, the transferring mechanism is not limited to the example and may be a conveyor belt and the like.

A main characteristic of the invention is that when sample pretreatment other than solid-phase extraction is conducted before the solid-phase extraction, the treatment is not conducted on a separate disk for the treatment. The sample pretreatment other than the solid-phase extraction means for example, concentration through liquid-liquid extraction or antigen-antibody reaction or the like. The "solid-phase extraction" is defined as a method for separating a component to be measured from impurities using the phenomenon that solutes contained in a solution or a suspension (a mobile phase) are adsorbed to a solid (a stationary phase) or pass through the solid depending on their affinities while the solution or the suspension passes through the solid. The "liquid-liquid extraction" is defined as a method for separating a component to be measured from impurities using the difference in solubility in another solvent between solutes contained in a solution or a suspension (a mobile phase) (mainly water and a nonpolar organic solvent). The "antigen-antibody reaction" is defined as a method for separating a component to be measured from impurities using the binding reaction between an antigen (the component to be measured) and an antibody.

FIRST EXAMPLE

The structure of the analyzer according to the first Example of the invention is explained using FIG. 1. FIG. 1 is a schematic plan view according to an Example of the analyzer of the invention. The analyzer of this Example has a sample disk (101), a solid-phase extraction cartridge disk (201), a reagent storage part (301), a solid-phase extraction solution storage part (401), a receiver disk (501), a container storage part (801), a detector (1001) and an analyzer controller (001).

The sample disk (101) is placed at the side of each of the container storage part (801), the solid-phase extraction cartridge disk (201) and the reagent storage part (301). On the sample disk (101), sample containers (102) containing samples are arranged on an endless track at predetermined intervals. A disposable container (901) can also be placed on the sample disk (101) in addition to the sample containers (102) as described below.

The sample disk (101) has a temperature control function and can store a sample and a pretreated sample solution without deterioration. The sample is a biological sample such as serum, plasma, whole blood, urine, saliva and cell tissues. A user of the analyzer dispenses a predetermined amount of a sample to a sample container (102) and sets the sample container (102) on the sample disk (101). The pretreated sample solution is a sample which has been subjected to pretreatment other than solid-phase extraction before the solid-phase extraction.

On the solid-phase extraction cartridge disk (201), solid-phase extraction cartridges (202) or disposable containers (901) can be each arranged on an endless track at predetermined intervals.

A probe 1 (701) has a gripper for holding a solid-phase extraction cartridge (202) or a disposable container (901). The probe 1 (701) can transfer a solid-phase extraction cartridge (202) or a disposable container (901) to the sample disk (101) or to the solid-phase extraction cartridge disk (201).

The track of the rotation of the probe 1 (701) crosses an opening in a solid-phase extraction cartridge storage part (802) for discharging the solid-phase extraction cartridges (202), an opening in a disposable-container storage part (803) for discharging the disposable containers (901), the track of the rotation of the sample disk (101) and the track of the rotation of the solid-phase extraction cartridge disk (201) each at at least one point. That is, the probe 1 (701) has an operating area which allows the probe 1 (701) to transfer a solid-phase extraction cartridge (202) in the solid-phase extraction cartridge storage part (802), a disposable container (901) in the disposable-container storage part (803), a disposable container (901) on the solid-phase extraction cartridge disk (201) and a disposable container (901) on the sample disk (101) while rotating.

A probe 2 (702) has a dispensing mechanism for sucking and discharging a liquid. The probe 2 (702) is placed at the side of each of the sample disk (101) and the solid-phase extraction cartridge disk (201). The track of the rotation of the probe 2 (702) crosses the track of the rotation of the sample disk (101) and the track of the rotation of the solid-phase extraction cartridge disk (201) each at at least one point.

The probe 2 (702) can transfer a sample in a sample container (102) set on the sample disk (101) to a solid-phase extraction cartridge (202) or a disposable container (901) set on the solid-phase extraction cartridge disk (201). Also, the probe 2 (702) can transfer a pretreated sample solution from a solid-phase extraction cartridge (202) or a disposable container (901) set on the solid-phase extraction cartridge disk (201) back to a sample container (102) or a disposable container (901) set on the sample disk (101).

Next, the solid-phase extraction cartridge (202) is explained using FIG. 2A and FIG. 2B. FIG. 2A is a schematic view of the solid-phase extraction cartridge according to an Example of the analyzer of the invention (addition of a solution). The solid-phase extraction cartridge (202) is composed of a solid-phase extraction packing material (2021), an upper filter (2022), a lower filter (2023) and a solid-phase extraction container (2024).

In the solid-phase extraction container (2024), the lower filter (2023), the solid-phase extraction packing material (2021) and the upper filter (2022) are disposed in this order from the bottom. The solid-phase extraction container (2024) has a structure in which the area of the top is larger than the area of the bottom and in which the top and the bottom are open. Thus, a solution can pass through from top to bottom without remaining in the solid-phase extraction container (2024).

As shown in FIG. 2A, a predetermined solution is added to the solid-phase extraction cartridge (202) using the probe 2 (702), a probe 3 (703) or a probe 4 (704). As shown in FIG. 2B, pressure is applied to the solid-phase extraction container (2024) from the top using a pressure-applying unit 1 (601), a pressure-applying unit 2 (602), a pressure-applying unit 3 (603), a pressure-applying unit 4 (604) or a pressure-applying unit 5 (605), and the solution is thus caused to pass through the solid-phase extraction packing material (2021) from top to bottom. The solid-phase extraction is conducted in this manner.

The disposable container (901) and a receiver container (502) on the receiver disk (501) each have a structure in which the area of the top is similar to the area of the bottom and in which the top is open while the bottom is closed. Thus, a solution can be kept in the disposable container (901) and in the receiver container (502).

The structure of the analyzer is explained again using FIG. 1. The container storage part (801) has the solid-phase extraction cartridge storage part (802) and the disposable-container storage part (803). The solid-phase extraction cartridge storage part (802) can store the solid-phase extraction cartridges (202). The disposable-container storage part (803) can store the disposable containers (901).

The reagent storage part (301) is placed at the side of each of the sample disk (101), the solid-phase extraction cartridge disk (201) and the solid-phase extraction solution storage part (101). Reagent containers (302) storing reagents are placed in the reagent storage part (301). The reagent containers (302) are arranged on a circle and share the same center in the reagent storage part (301). The reagent containers (302) contain reagents such as an internal standard material of a component to be measured, a proteolytic agent and an antibody reagent. The reagent storage part (301) has a temperature control function and can store the reagents without deterioration.

The probe 3 (703) has a dispensing mechanism for sucking and discharging a liquid. The probe 3 (703) is placed at the side of each of the solid-phase extraction cartridge disk (201) and the reagent storage part (301). The track of the rotation of the probe 3 (703) crosses the track of the rotation of the sample disk (101) and the track of the rotation of the solid-phase extraction cartridge disk (201) each at at least one point and crosses all of the reagent containers (302) set in the reagent storage part (301). The probe 3 (703) can transfer a reagent in a reagent container (302) set in the reagent storage part (301) to a sample container (102) or a disposable container (901) set on the sample disk (101) and to a solid-phase extraction cartridge (202) or a disposable container (901) set on the solid-phase extraction cartridge disk (201).

The solid-phase extraction solution storage part (401) is placed at the side of each of the reagent storage part (301) and the solid-phase extraction cartridge disk (201). Solid-phase extraction solution containers (402) storing solid-phase extraction solutions are placed in the solid-phase extraction solution storage part (401). The solid-phase extraction solution containers (402) are arranged on a circle and share the same center in the solid-phase extraction solution storage part (401). The solid-phase extraction solution containers (402) contain solid-phase extraction solutions. The solid-phase extraction solutions are an organic solvent, an aqueous solvent or a mixture of an organic solvent and an aqueous solvent. The solid-phase extraction solutions are used for a conditioning step, an equilibration step, a washing step and an elution step for the solid-phase extraction packing material (2021) in a solid-phase extraction cartridge (202).

The probe 4 (704) has a dispensing mechanism for sucking and discharging a liquid. The probe 4 (704) is placed at the side of each of the solid-phase extraction cartridge disk (201) and the solid-phase extraction solution storage part (401). The track of the rotation of the probe 4 (704) crosses the track of the rotation of the solid-phase extraction cartridge disk (201) at at least one point and crosses all of the solid-phase extraction solution containers (402) set in the solid-phase extraction solution storage part (401). The probe 4 (704) can transfer a solid-phase extraction solution in a solid-phase extraction solution container (402) set in the solid-phase extraction solution storage part (401) to a solid-phase extraction cartridge (202) set on the solid-phase extraction cartridge disk (201).

The receiver disk (501) is placed under the solid-phase extraction cartridge disk (201). On the receiver disk (501), receiver containers (502) which each can capture an eluate eluted from the bottom of a solid-phase extraction cartridge (202) are arranged on an endless track at predetermined intervals. The track of the rotation of the solid-phase extraction cartridges (202) on the solid-phase extraction cartridge disk (201) crosses the track of the rotation of the receiver containers (502) on the receiver disk (501) at at least one point. This structure creates a space above the receiver containers (502) where the receiver containers (502) do not overlap with the solid-phase extraction cartridge disk (201), and the access to an eluate after the solid-phase extraction is thus easy.

The analyzer controller (001) controls the components of the analyzer and is composed of an information processor such as a personal computer. The analyzer controller (001) has a central processing device, an auxiliary memory device, a main memory device, a display unit and an input unit. For example, the central processing device is composed of a processor (also called an operation unit) such as CPU (central processing unit). For example, the auxiliary memory device is a hard disk, and the main memory device is a memory. The display unit is a display or the like, and the input unit is a keyboard, a pointing device (a mouse or the like) or the like.

The structure of the pressure-applying unit 1 is explained using FIG. 3. The pressure-applying unit 1 (601) has a syringe pump (6011) capable of drawing gas and pressurizing, an air filter (6014) for removing foreign matters in the gas drawn into the syringe pump (6011), a junction (6016) for sending pressurized gas to a solid-phase extraction cartridge (202), a three-way solenoid valve (6015) capable of controlling the switching of the passages connecting the syringe pump (6011), the air filter (6014) and the junction (6016), a flowmeter (6012) which is located between the three-way solenoid valve (6015) and the junction (6016) and which measures the flow rate of the gas sent to the junction (6016) and a pressure gauge (6013) which is located between the three-way solenoid valve (6015) and the junction (6016) and which measures the pressure of the gas sent to the junction (6016).

During the operation of the pressure-applying unit 1 (601), the syringe pump (6011) draws in the drawing direction while the ports of the three-way solenoid valve (6015) at the syringe pump (6011) side and at the air filter (6014) side are open and the port of the three-way solenoid valve (6015) at the junction (6016) side is closed. Next, while the ports of the three-way solenoid valve (6015) at the syringe pump (6011) side and at the junction (6016) side are open and the port of the three-way solenoid valve (6015) at the air filter (6014) side is closed, the syringe pump (6011) is pressurized, and the gas is thus pushed into the junction (6016). Pressure is applied to the solid-phase extraction cartridge (202) in this manner.

The pressure-applying unit 2 (602), the pressure-applying unit 3 (603), the pressure-applying unit 4 (604) and the pressure-applying unit 5 (605) each have the same structure as that of the pressure-applying unit 1 (601). The pressure-applying unit 1 (601), the pressure-applying unit 2 (602), the pressure-applying unit 3 (603), the pressure-applying unit 4 (604) and the pressure-applying unit 5 (605) can conduct the pressure application operation independently from each other and at the same time.

The structure of the detector (1001) is explained using FIG. 4. The detector (1001) has a solvent (10011), a solvent-sending pump (10012) for sending the solvent (10011), a six-way valve (10013), a sample loop (10014) for measuring a set amount of a solid-phase extracted sample, a sample introduction probe (10015) for introducing the solid-phase extracted sample after the solid-phase extraction from the receiver container (502) set on the receiver disk (501) into a passage, a three-way valve (10016) for switching the passage and a liquid waste passage (10017), an ion source (10018) for ionizing the solid-phase extracted sample, which is a liquid, by applying high voltage at a high temperature at the passage outlet and introducing the solid-phase extracted sample into a mass spectrometer (10019) and the mass spectrometer (10019) for measuring the solid-phase extracted sample. Here, the "solid-phase extracted sample" is defined as a solution which has been subjected to the sample pretreatment and the solid-phase extraction or to the solid-phase extraction.

In this Example, electrospray ionization (ESI) was used as the ionization method of the solid-phase extracted sample by the ion source. Another ionization method is atomospheric pressure chemical ionization (APCI) or the like.

In this Example, a component to be measured is analyzed using a triple quadrupole mass spectrometer as the mass spectrometer (10019) in the SRM (selected reaction monitoring) mode. As the mass spectrometer (10019), other types of mass spectrometer such as a quadrupole mass spectrometer and an ion trap mass spectrometer may also be used.

Next, the processing operations of the analyzer of an Example of the invention are explained using FIG. 5. The processing operations can be classified into a case where a sample pretreatment operation is conducted and a case where no sample pretreatment operation is conducted. When a sample pretreatment operation is conducted, a sample pretreatment operation (S002) is conducted after the start of the operations (S001), and a solid-phase extraction operation (S003) is conducted. Then, measurement at the detector (1001) (S005) is conducted, followed by the end of the operations.

When no sample pretreatment operation is conducted, the solid-phase extraction operation (S003) is conducted after the start of the operations (S001), and the measurement at the detector (1001) (S005) is conducted, followed by the end of the operations. The analyzer controller (001) can determine whether or not a sample pretreatment operation is conducted. Information on the processing operations fixed for the respective components to be measured is stored in a memory device of the analyzer controller (001). When the information on a component to be measured is input to the analyzer controller (001) through the input unit, the analyzer controller (001) can determine whether or not a sample pretreatment operation is conducted based on the information on the processing operations.

Processing operations are explained using 25-hydroxyvitamin $D_3$ [$25(OH)D_3$] as an example component to be measured which is subjected to a sample pretreatment operation. Vitamin D is fat-soluble vitamin which has been found as an antirachitic factor, and its active metabolite is a kind of steroid hormone which regulates biological calcium via the nuclear D receptor. Vitamin $D_2$ to vitamin $D_7$ having different side chain structures at the 17β-position are known as vitamin D, and vitamin $D_3$ is the major vitamin D in humans. Vitamin $D_3$ which has been synthesized biologically from 7-dehydrocholesterol in the skin or taken from foods is metabolized in the liver into 25-hydroxyvitamin $D_3$, which binds to the D-binding protein in the blood and circulates in the body. The measurement of $25(OH)D_3$ is important for differential diagnosis of diseases accompanied by rickets, malignant tumors and the like.

However, the blood level of $25(OH)D_3$ is extremely low, namely at the ng/mL level, and the structure thereof is very similar to that of the metabolite. Thus, the analysis of $25(OH) D_3$ requires extremely high sensitivity and selectivity. At present, $25(OH)D_3$ is purified using serum or plasma as a sample by two steps: (1) dissociation of $25(OH)D_3$ from the D-binding protein; and (2) solid-phase extraction or liquid-liquid extraction. In general, LC/MS (liquid chromatography-mass spectrometry) is used for measuring $25(OH) D_3$ after the purification. The (1) dissociation in the purification is defined as breakage of the bond of the D-binding protein and $25(OH)D_3$ by adding a proteolytic agent. The proteolytic agent is an organic solvent such as methanol, an alkaline compound such as sodium hydroxide, an alkali metal hydroxide such as zinc sulfate or the like.

FIG. 6A and FIG. 6B are figures explaining the processing operations including a sample pretreatment operation and the processing operations including no sample pretreatment operation. FIG. 6A is a figure explaining the processing operations including a sample pretreatment operation. FIG. 6B is a figure explaining the processing operations including no sample pretreatment operation.

A case where a sample pretreatment operation is conducted is explained using FIG. 1, FIG. 5 and FIG. 6A. First, a user of the analyzer inputs the information that $25(OH)D_3$ is measured to the analyzer controller (001) through the input unit. The information on the processing operations of the $25(OH)D_3$ measurement is stored in the memory device of the analyzer controller (001), and the processing operations are output. Since the processing operations of the $25(OH)D_3$ measurement include a sample pretreatment operation, the sample pretreatment operation (S002) is conducted after the start of the operations (S001). Then, the solid-phase extraction operation (S003) is conducted, and the measurement at the detector (1001) (S005) is conducted, followed by the end of the operations (FIG. 5).

Next, the processing operation of the sample pretreatment operation (S002) is explained. First, the solid-phase extraction cartridge disk (201) rotates to a predetermined position. At the same time, the probe 1 (701) supplies a disposable container (901) stored in the disposable-container storage part (803) to the solid-phase extraction cartridge disk (201).

Then, the sample disk (101) and the solid-phase extraction cartridge disk (201) rotate to predetermined positions. At the same time, the probe 2 (702) supplies a sample stored in a sample container (102) on the sample disk (101) to the disposable container (901) on the solid-phase extraction cartridge disk (201). Then, the solid-phase extraction cartridge disk (201) rotates to a predetermined position. At the same time, the probe 3 (703) supplies the internal standard material stored in the reagent storage part (301) to the disposable container (901).

Subsequently, the probe 3 (703) supplies the proteolytic agent stored in a reagent container (302) in the reagent storage part (301) to the disposable container (901). Then, the sample disk (101) and the solid-phase extraction cartridge disk (201) rotate to predetermined positions. At the same time, the probe 1 (701) transfers the disposable container (901) on the solid-phase extraction cartridge disk (201) to the sample disk (101).

The sample, the internal standard material and the proteolytic agent may be mixed in a disposable container (901) set on the sample disk (101) instead of in a disposable container (901) set on the solid-phase extraction cartridge disk (201) as in this Example. Also, the sample may be supplied to a disposable container (901) set on the sample disk (101) instead of to a disposable container (901) set on the solid-phase extraction cartridge disk (201) as in this Example.

The probe 2 (702), the probe 3 (703) and the probe 4 (704) are washed with distilled water after every suction/discharge using a washing port (which is not shown in the drawings). Although this Example employs a method of washing the probes after every suction/discharge, a method of changing disposable pipette tips after every suction/discharge may also be used.

Next, the processing operation of the solid-phase extraction operation (S003) is explained. When a sample pretreatment operation is conducted, the solid-phase extraction operation (S003) includes a conditioning step operation (S0031), an equilibration step operation (S0032), a pretreated sample solution introduction step operation (S0033A), a washing step operation (S0034) and an elution step operation (S0035).

The conditioning step operation (S0031) is explained. By adding a conditioning solution (methanol in this Example) to a solid-phase extraction cartridge (202), the solid-phase extraction packing material (2021) in the solid-phase extraction cartridge (202) is conditioned.

In the processing operation, first, the solid-phase extraction cartridge disk (201) rotates to a predetermined position. At the same time, the probe 1 (701) supplies a solid-phase extraction cartridge (202) stored in the solid-phase extraction cartridge storage part (802) to the solid-phase extraction cartridge disk (201). Then, the solid-phase extraction cartridge disk (201) rotates to a predetermined position. At the same time, the probe 4 (704) supplies the conditioning solution in a solid-phase extraction solution container (402) stored in the solid-phase extraction solution storage part (401) to the solid-phase extraction cartridge (202). After the solid-phase extraction cartridge disk (201) rotates and the solid-phase extraction cartridge (202) is transferred to under the pressure-applying unit 1 (601), the pressure-applying unit 1 (601) applies pressure. The conditioning step operation (S0031) finishes when the conditioning solution has passed through the solid-phase extraction packing material (2021).

The equilibration step operation (S0032) is explained. By adding an equilibration solution (distilled water in this Example) to the solid-phase extraction cartridge (202) after the conditioning step operation (S0031), the solid-phase extraction packing material (2021) in the solid-phase extraction cartridge (202) is equilibrated.

In the processing operation, first, the solid-phase extraction cartridge disk (201) rotates to a predetermined position. At the same time, the probe 4 (704) supplies the equilibration solution in a solid-phase extraction solution container (402) stored in the solid-phase extraction solution storage part (401) to the solid-phase extraction cartridge (202). After the solid-phase extraction cartridge disk (201) rotates and the solid-phase extraction cartridge (202) is transferred to under the pressure-applying unit 2 (602), the pressure-applying unit 2 (602) applies pressure. The equilibration step operation (S0032) finishes when the equilibration solution has passed through the solid-phase extraction packing material (2021).

The pretreated sample solution introduction step operation (S0033A) is explained. By adding a pretreated sample solution to the solid-phase extraction cartridge (202) after the equilibration step operation (S0032), the component to be measured in the pretreated sample solution is adsorbed to the solid-phase extraction packing material (2021) in the solid-phase extraction cartridge (202).

In the processing operation, first, the solid-phase extraction cartridge disk (201) and the sample disk (101) rotate to predetermined positions. At the same time, the probe 2 (702) supplies a predetermined volume of the pretreated sample solution after the reaction in a disposable container (901) on the sample disk (101) to the solid-phase extraction cartridge (202) after the equilibration step operation (S0032). After the solid-phase extraction cartridge disk (201) rotates and the solid-phase extraction cartridge (202) is transferred to under the pressure-applying unit 3 (603), the pressure-applying unit 3 (603) applies pressure. The pretreated sample solution introduction step operation (S0033A) finishes when the pretreated sample solution has passed through the solid-phase extraction packing material (2021).

The washing step operation (S0034) is explained. By adding a washing solution (distilled water in this Example) to the solid-phase extraction cartridge (202) after the pretreated sample solution introduction step operation (S0033A), the solid-phase extraction packing material (2021) in the solid-phase extraction cartridge (202) is washed.

In the processing operation, first, the solid-phase extraction cartridge disk (201) rotates to a predetermined position. At the same time, the probe 4 (704) supplies the washing solution in a solid-phase extraction solution container (402) stored in the solid-phase extraction solution storage part (401) to the solid-phase extraction cartridge (202). After the solid-phase extraction cartridge disk (201) rotates and the solid-phase extraction cartridge (202) is transferred to under the pressure-applying unit 4 (604), the pressure-applying unit 4 (604) applies pressure. The washing step operation (S0034) finishes when the washing solution has passed through the solid-phase extraction packing material (2021).

The elution step operation (S0035) is explained. In the elution step, by adding an eluent (methanol in this Example) to the solid-phase extraction cartridge (202) after the washing step operation (S0034), the component to be measured is eluted from the solid-phase extraction packing material (2021) in the solid-phase extraction cartridge (202).

In the processing operation, first, the receiver disk (501) rotates to a predetermined position, and a receiver container (502) is supplied using a probe (which is not shown in the drawings). Then, the solid-phase extraction cartridge disk (201) rotates to a predetermined position. At the same time, the probe 4 (704) supplies the eluent in a solid-phase extraction solution container (402) stored in the solid-phase extraction solution storage part (401) to the solid-phase extraction cartridge (202). After the solid-phase extraction cartridge disk (201) and the receiver disk (501) rotate and the solid-phase extraction cartridge (202) and the receiver container (502) are transferred to under the pressure-applying unit 5 (605), the pressure-applying unit 5 (605) applies pressure. The elution step operation (S0035) finishes when the eluent has passed through the solid-phase extraction packing material (2021) and the component to be measured has been eluted from the solid-phase extraction packing material (2021) into the receiver container (502).

The measurement at the detector (1001) (S005) is explained. The solid-phase extracted sample in the receiver container (502) is introduced to the passage of the detector (1001) by the sample introduction probe (10015). Only a set amount (30 μL in this Example) of the solid-phase extracted sample is measured by the sample loop (10014) in the passage and reaches the ion source (10018) by switching of the six-way valve (10013) and the three-way valve (10016). The solid-phase extracted sample is subjected to a high temperature and high voltage in the ion source (10018) and introduced to the mass spectrometer (10019) in the vaporized state, and the component to be measured is measured.

Next, the processing operations are explained using theophylline as an example component to be measured which is not subjected to any sample pretreatment operation. Theophylline is a kind of alkaloid of bitter components contained in tea leaves and is an agent for treating respiratory diseases such as bronchial asthma and chronic bronchitis.

A case where no sample pretreatment operation is conducted is explained using FIG. 1, FIG. 5 and FIG. 6B. First, a user of the analyzer inputs the information that theophylline is measured to the analyzer controller (001). The information on the processing operations of the theophylline measurement is stored in the memory device of the analyzer controller (001), and the processing operations are output. Since the processing operations of the theophylline measurement do not include any sample pretreatment operation, the solid-phase extraction operation (S003) is conducted after the start of the operations (S001). Then, the measurement at the detector (1001) (S005) is conducted, followed by the end of the operations (FIG. 5).

When no sample pretreatment operation is conducted, the solid-phase extraction operation (S003) includes the conditioning step operation (S0031), the equilibration step operation (S0032), a sample introduction step operation (S0033B), the washing step operation (S0034) and the elution step operation (S0035). When no sample pretreatment operation is conducted, the conditioning step operation (S0031), the equilibration step operation (S0032), the washing step operation (S0034), the elution step operation (S0035) and the measurement at the detector (1001) (S005) are the same as those of the case where no sample pretreatment operation is conducted. Thus, the sample introduction step operation (S0033B) is explained below.

In the sample introduction step operation (S0033B), by adding a sample to a solid-phase extraction cartridge (202) after the equilibration step operation (S0032), the component to be measured in the sample is adsorbed to the solid-phase extraction packing material (2021) in the solid-phase extraction cartridge (202).

In the processing operation, first, the solid-phase extraction cartridge disk (201) and the sample disk (101) rotate to predetermined positions. At the same time, the probe 2 (702) supplies a predetermined volume of the sample in a sample container (102) on the sample disk (101) to the solid-phase extraction cartridge (202) after the equilibration step operation (S0032). After the solid-phase extraction cartridge disk (201) rotates and the solid-phase extraction cartridge (202) is transferred to under the pressure-applying unit 3 (603), the pressure-applying unit 3 (603) applies pressure. The sample introduction step operation (S0033B) finishes when the sample has passed through the solid-phase extraction packing material (2021).

In this manner, the analyzer can randomly measure a sample which is subjected to a sample pretreatment operation and a sample which is not subjected to the sample pretreatment operation. FIG. 7A to FIG. 7E are figures explaining the scheduling of the processing operations in the analyzer of an Example of the invention, where components to be measured which are subjected to a sample pretreatment operation and those which are not subjected to the sample pretreatment operation are mixed. For example, the scheduling of a case where a user of the analyzer inputs the information on 10 samples to the analyzer controller (001) is explained.

For example, in the schedule shown in FIG. 7A to FIG. 7E, the first measurement includes a sample pretreatment operation (hereinafter referred to as "with"), and the second measurement does not include the sample pretreatment operation (hereinafter referred to as "without"). The third, fourth, fifth, sixth, seventh, eighth, ninth and tenth measurement operations are "with", "with", "without", "without", "with", "with", "with" and "without", respectively.

The reaction period in the sample pretreatment operation (S002) of this Example requires 20 minutes. In the solid-phase extraction operation (S003), each of the conditioning step operation (S0031), the equilibration step operation (S0032), the pretreated sample solution introduction step operation (S0033A), the sample introduction step operation (S0033B), the washing step operation (S0034) and the elution step operation (S0035) requires one minute.

In the solid-phase extraction operation (S003), samples can be processed in parallel at the same time in the conditioning step operation (S0031), the equilibration step operation (S0032), the pretreated sample solution introduction step operation (S0033A) or the sample introduction step operation (S0033B), the washing step operation (S0034) and the elution step operation (S0035).

Therefore, to process the 10 samples in the shortest period, the start of the operations (S001) of the measurement of all the samples which are subjected to the sample pretreatment operation is made prior to that of the samples which are not subjected to the sample pretreatment operation. During the reaction period in the sample pretreatment operation (S002), the operations of the other samples which are not subjected to the sample pretreatment operation are started (S001). In this manner, the processing of the 10 samples finishes in 30 minutes.

As described above, the information on the processing operations of the samples is stored in the memory device of the analyzer controller (001) in advance. Thus, when the information on the samples is input, the analyzer controller (001) can determine whether or not a sample pretreatment operation is conducted using the information on the processing operations of the samples and automatically output the schedule of the input samples. For example, as described above, the analyzer controller (001) may arrange the schedule in such a way that the operations of the samples which are subjected to a sample pretreatment operation are started (S001) prior to those of the samples which are not subjected to the sample pretreatment operation. The analyzer controller (001) may arrange the schedule in such a way that the operations of the samples which are not subjected to the sample pretreatment operation are started (S001) during the reaction period in the sample pretreatment operation (S002).

The scheduling of a case where the number of samples is large and the operations of the other samples which are not subjected to the sample pretreatment operation do not finish during the reaction period in the sample pretreatment operation (S002), for example, is explained. In this case, the unfinished samples which are not subjected to the sample pretreatment operation are scheduled to be processed later and processed in parallel with the solid-phase extraction operation (S003) of the samples which are subjected to the sample pretreatment operation.

As explained above in this Example, the analyzer of the invention has a mechanism for conducting different kinds of processing on a single disk. With the mechanism, an analyzer which has a reduced number of disks, which maintains the throughput and which has a small apparatus area can be provided.

In PTL 1, which relates to a conventional technique, an item with a low blood level is analyzed after conducting purification twice using a first disk and a second disk. Thus, in the conventional technique, a separate disk is necessary when sample pretreatment other than solid-phase extraction is conducted, and the area of the entire apparatus becomes large. In such an analyzer, for example, the numbers of containers which can be installed on the disks have to be increased to improve the throughput, and as a result, the area of the entire apparatus sometimes becomes large. On the other hand, when the area of the entire apparatus is reduced, the numbers of containers which can be installed on the disks have to be reduced, and the throughput sometimes decreases. In this Example, since different kinds of processing can be conducted on the sample disk (101) or on the solid-phase extraction cartridge disk (201), the number of disks can be reduced, and the throughput can be maintained. Also, the apparatus area can be reduced. In addition, the analyzer controller (001) can most suitably arrange the schedule of the measurement period of the input samples based on the information as to whether or not a sample pretreatment operation is conducted.

SECOND EXAMPLE

A main characteristic of the second Example is that when sample post-treatment other than the solid-phase extraction is conducted after the solid-phase extraction, the treatment is not conducted on a separate disk for the treatment. The sample post-treatment other than the solid-phase extraction is derivatization for example.

The "derivatization" is defined as a modification of a component to be measured through introduction of a functional group, oxidation, reduction, replacement of an atom or the like, which does not largely change the structure and the properties. The derivatization is conducted to improve the ionization efficiency when the sensitivity of LC/MS is insufficient. As the derivatization reagent, 4-phenyl-1,2,4-triazoline-3,5-dione (PTAD), the 4-position analogue thereof or the like is used.

The structure of the analyzer of this Example is explained using FIG. 8. FIG. 8 is a schematic plan view according to an Example of the analyzer of the second Example of the invention. The part of the structure of the analyzer of this Example which is different from that of the first Example is explained. The analyzer is different from that of the first Example in that a probe 5 (705) is provided, and the other components of the analyzer are the same as those of the first Example.

The probe 5 (705) has a dispensing mechanism for sucking and discharging a liquid. The probe 5 (705) is placed at the side of each of the solid-phase extraction cartridge disk (201) and the receiver disk (501). The track of the rotation of the probe 5 (705) crosses the track of the rotation of the solid-phase extraction cartridge disk (201) and the track of the rotation of the receiver disk (501) each at at least one point.

The probe 5 (705) supplies a component to be measured which has been eluted from a solid-phase extraction packing material (2021) into a receiver container (502) on the receiver disk (501) to a disposable container (901) set on the solid-phase extraction cartridge disk (201). Because the receiver disk (501) is located under the solid-phase extraction cartridge disk (201), the probe 5 (705) can also move up and down.

The probe 5 (705) may have a mechanism capable of supplying a receiver container (502) set on the receiver disk (501) to the solid-phase extraction cartridge disk (201). In this case, on the solid-phase extraction cartridge disk (201), the component to be measured in the receiver container (502) set on the solid-phase extraction cartridge disk (201) may be supplied to a disposable container (901) set on the solid-phase extraction cartridge disk (201) for example using a probe.

Next, the processing operations according to an Example of the analyzer of the second Example of the invention are explained using FIG. 9. The processing operations can be classified into a case where a sample pretreatment operation is conducted and a case where no sample pretreatment operation is conducted.

When the sample pretreatment operation is conducted, the sample pretreatment operation (S002) is conducted after the start of the operations (S001), and the solid-phase extraction operation (S003) is conducted. When the sample pretreatment operation is conducted, the processing operations can be further classified into a case where a sample post-treatment operation is conducted and a case where no sample post-treatment operation is conducted. When the sample post-treatment operation is conducted, after the start of the operations (S001), the sample pretreatment operation (S002), the solid-phase extraction operation (S003), a sample post-treatment operation (S004) and the measurement by the detector (1001) (S005) are conducted. When the sample post-treatment operation is not conducted, after the start of the operations (S001), the sample pretreatment operation (S002), the solid-phase extraction operation (S003) and the measurement by the detector (1001) (S005) are conducted.

When the sample pretreatment operation is not conducted, the solid-phase extraction operation (S003) is conducted after the start of the operations (S001). When the sample pretreatment operation is not conducted, the processing operations can be further classified into a case where a sample post-treatment operation is conducted and a case where no sample post-treatment operation is conducted. When the sample post-treatment operation is conducted, after the start of the operations (S001), the solid-phase extraction operation (S003), the sample post-treatment operation (S004) and the measurement by the detector (1001) (S005) are conducted. When the sample post-treatment operation is not conducted, after the start of the operations (S001), the solid-phase extraction operation (S003) and the measurement by the detector (1001) (S005) are conducted.

Information on the processing operations fixed for the respective components to be measured is stored in the analyzer controller (001). When the information on a component to be measured is input, the analyzer controller (001) can determine whether or not a sample pretreatment operation and a sample post-treatment operation are conducted using the information on the processing operations and determine the measurement schedule.

Processing operations are explained using metabolites of 25-hydroxyvitamin $D_3$ [25(OH)$D_3$] as example components to be measured which are subjected to a sample pretreatment operation and to a sample post-treatment operation.

25(OH)$D_3$ is hydroxylated at the 1α-position in the kidney when the serum calcium level becomes the normal level (90 to 100 ng/mL) or lower and metabolized into 1α,25-dihydroxyvitamin D3 [1α,25(OH)$_2D_3$], which is active $D_3$. When the blood calcium level is recovered, however, the hydroxylation at the 1α-position is inhibited, and 25(OH)$D_3$ is metabolized mainly into 24R,25-dihydroxyvitamin D3 [24,25 (OH)$_2D_3$].

The measurement of 1α,25(OH)$_2D_3$ and 24,25(OH)$_2D_3$, which are metabolites of 25(OH)$D_3$, is important for differential diagnosis of diseases accompanied by malignant tumors and disorders of vitamin $D_3$ metabolism. However, the blood levels of 1α,25(OH))$_2D_3$ and 24,25(OH)$_2D_3$ are extremely low, namely at the pg/mL level, and the structures are very similar to each other. Thus, the analysis thereof requires extremely high sensitivity and selectivity. At present, 1α,25(OH)$_2D_3$ and 24,25(OH)$_2D_3$ are purified using serum or plasma as a sample by three steps: (1) dissociation of 1α,25(OH)$_2D_3$ and 24,25(OH)$_2D_3$ from the D-binding protein; (2) solid-phase extraction or liquid-liquid extraction; and (3) derivatization. In general, LC/MS is used for measuring 1α,25(OH)$_2D_3$ and 24,25(OH)$_2D_3$ after the purification.

The sample pretreatment operation (S002), the solid-phase extraction operation (S003) and the measurement by the detector (1001) (S005) are the same as those of the example described above. Thus, the sample post-treatment operation (S004) is explained next.

In the sample post-treatment operation (S004), first, the solid-phase extraction cartridge disk (201) rotates to a predetermined position. At the same time, the probe 1 (701) supplies a disposable container (901) stored in the disposable-container storage part (803) to the solid-phase extraction cartridge disk (201). At the same time, the probe 5 (705) transfers the components to be measured which have been eluted from a solid-phase extraction packing material (2021)

into a receiver container (502) on the receiver disk (501) to the disposable container (901) on the solid-phase extraction cartridge disk (201).

Then, the solid-phase extraction cartridge disk (201) rotates to a predetermined position. At the same time, the probe 3 (703) supplies the derivatization reagent stored in the reagent storage part (301) to the disposable container (901) on the solid-phase extraction cartridge disk (201). Subsequently, the sample disk (101) and the solid-phase extraction cartridge disk (201) rotate to predetermined positions. At the same time, the probe 1 (701) transfers the disposable container (901) on the solid-phase extraction cartridge disk (201) to the sample disk (101). The derivatization reaction is conducted for a predetermined period (30 minutes in this Example) in the disposable container (901) on the sample disk (101).

The derivatization reagent may be added in a disposable container (901) set on the sample disk (101) instead of in a disposable container (901) set on the solid-phase extraction cartridge disk (201) as in this Example. In this case, before adding the derivatization reagent, the probe 1 (701) may transfer the disposable container (901) on the solid-phase extraction cartridge disk (201) to the sample disk (101).

Also, the derivatization reaction may be conducted in a disposable container (901) on the solid-phase extraction cartridge disk (201). In this case, the disposable container (901) on the solid-phase extraction cartridge disk (201) is not transferred to the sample disk (101).

After the derivatization reaction finishes, the sample disk (101) and the solid-phase extraction cartridge disk (201) rotate to predetermined positions. The probe 1 (701) transfers the disposable container (901) on the sample disk (101) to the solid-phase extraction cartridge disk (201).

Then, the receiver disk (501) rotates to a predetermined position, and a receiver container (502) is supplied using a probe (which is not shown in the drawings). The sample disk (101) and the solid-phase extraction cartridge disk (201) rotate to predetermined positions. At the same time, the probe 5 (705) transfers the derivatized compounds of the substances to be measured after the derivatization from the disposable container (901) on the solid-phase extraction cartridge disk (201) to the receiver container (502) on the receiver disk (501).

In this Example, processing operations have been explained using metabolites of 25-hydroxyvitamin $D_3$ [25 (OH) $D_3$] as example components to be measured which are subjected to a sample pretreatment operation and to a sample post-treatment operation, but the analyzer can also analyze a component to be measured which is not subjected to any sample pretreatment operation and is subjected to a sample post-treatment operation.

In this manner, the analyzer can randomly measure samples considering whether or not a sample pretreatment operation is conducted and whether or not a sample pretreatment operation is conducted. FIG. 10A to FIG. 10E are figures explaining the scheduling of the processing operations of the analyzer of an Example of the invention, where components to be measured which are subjected to a sample pretreatment operation, those which are not subjected to the sample pretreatment operation, those which are subjected to a sample post-treatment operation and those which are not subjected to the sample post-treatment operation are mixed. For example, the scheduling of a case where a user of the analyzer inputs the information on 10 samples to the analyzer controller (001) is explained.

For example, the first measurement includes a sample pretreatment operation and a sample post-treatment operation (hereinafter referred to as "with/with"), and the second measurement does not include the sample pretreatment operation and includes the sample post-treatment operation (hereinafter referred to as "without/with"). The third measurement includes the sample pretreatment operation and does not include the sample post-treatment operation (hereinafter referred to as "with/without"), and the fourth measurement is "with/with". The fifth measurement is "without/with", and the sixth measurement is "without/with". The seventh measurement is "with/with", and the eighth measurement is "with/without". The ninth measurement is "with/without", and the tenth measurement is "without/with".

To process the 10 samples in the shortest period, the operations of all the samples which are subjected to the sample pretreatment operation are started (S001) first. During the reaction period in the sample pretreatment operation (S002), the operations of the other samples which are not subjected to the sample pretreatment operation are started (S001). As shown in FIG. 10A to FIG. 10E, since the period of the sample post-treatment operation (S004) is short, it is preferred that the operations including the sample pretreatment operation are mainly scheduled with priority.

As described above, the information on the processing operations of the samples is stored in the memory device of the analyzer controller (001). Thus, when the information on the samples is input, the analyzer controller (001) can determine whether or not a sample pretreatment operation and a sample post-treatment operation are conducted using the information on the processing operations of the samples and automatically output the schedule of the input samples. For example, as described above, the analyzer controller (001) may arrange the schedule in such a way that the operations of the samples which are subjected to the sample pretreatment operation are started (S001) prior to those of the samples which are not subjected to the sample pretreatment operation. The analyzer controller (001) may arrange the schedule in such a way that the operations of the samples which are not subjected to the sample pretreatment operation are started (S001) during the reaction period in the sample pretreatment operation (S002).

As explained above in this Example, since the invention has a mechanism for conducting different kinds of processing on a single disk, an analyzer which has a reduced number of disks, which maintains the throughput and which has a small apparatus area can be provided.

In the conventional techniques, an operator used to manually conduct sample post-treatment, and the operations including the sample post-treatment could not be automated. According to this Example, since a component to be measured in a receiver container (502) on the receiver disk (501) can be transferred to the solid-phase extraction cartridge disk (201), the sample post-treatment can also be automated. Also, since an operator used to manually conduct the sample post-treatment in the conventional techniques, automated scheduling has been impossible. However, the analyzer controller (001) can determine whether or not a sample pretreatment operation and a sample post-treatment operation are conducted and automatically arrange the schedule of the input samples.

The invention is not limited to the Examples described above but includes various modified examples. For example, the Examples have been described in detail to simply explain the invention, and the invention is not necessarily limited to those having all the explained components. Also, a part of the components of an Example is sometimes replaced with a component of another Example, and a component of an Example may be added to the components of another Example. Furthermore, another component may be added to a part of the components of each Example, and a part of the components of each Example may be removed or replaced.

In the structures of the above examples, the probe 1 (701) transfers a disposable container (901) on the solid-phase extraction cartridge disk (201) to the sample disk (101), but the invention is not limited to the examples. For example, a sample container (102) and a disposable container (901) may be placed on the sample disk (101) in advance. Also, a disposable container (901) on the solid-phase extraction cartridge disk (201) may be transferred to the receiver disk (501) instead of to the sample disk (101). In this case, the sample pretreatment is conducted on the receiver disk. This structure only requires a probe for transferring a disposable container (901) between the solid-phase extraction cartridge disk (201) and the receiver disk (501).

A part or the whole of the functions of the analyzer controller (001), of the processing unit, of the processing means and the like may be carried out by hardware for example by designing with an integrated circuit. Moreover, the above components, the above functions and the like may be carried out by software using a processor which reads and executes the programs for carrying out the functions. The information on the programs, the tables, the files and the like for carrying out the functions can be stored in a memory device such as a memory, a hard disk and SSD (SoliD State Drive) or in a storage medium such as an IC card, an SD card and a DVD.

In the above Examples, only the control lines and the information lines which are thought to be necessary for the explanations are shown, but not all of the control lines and the information lines which are necessary for the product are shown. It may be regarded that almost all of the components are connected to each other in practice.

REFERENCE SIGNS LIST

001: Analyzer controller
101: Sample disk
102: Sample container
201: Solid-phase extraction cartridge disk
202: Solid-phase extraction cartridge
301: Reagent storage part
302: Reagent container
401: Solid-phase extraction solution storage part
402: Solid-phase extraction solution container
501: Receiver disk
502: Receiver container
602: Pressure-applying unit 1
602: Pressure-applying unit 2
603: Pressure-applying unit 3
604: Pressure-applying unit 4
605: Pressure-applying unit 5
701: Probe 1
702: Probe 2
703: Probe 3
704: Probe 4
705: Probe 5
801: Container storage part
802: Solid-phase extraction cartridge storage part
803: Disposable-container storage part
901: Disposable container
1001: Detector
10011: Solvent
10012: Solvent-sending pump
10013: Six-way valve
10014: Sample loop
10015: Sample introduction probe
10016: Three-way valve
10017: Liquid waste passage
10018: Ton source
10019: Mass spectrometer
2021: Solid-phase extraction packing material
2022: Upper filter
2023: Lower filter
2024: Solid-phase extraction container
6011: Syringe pump
6012: Flowmeter
6013: Pressure gauge
6014: Air filter
6015: Three-way solenoid valve
6016: Junction
S001: Start of operations
S002: Sample pretreatment operation
S003: Solid-phase extraction operation
S005: Measurement at detector
S0031: Conditioning step operation
S0032: Equilibration step operation
S0033A: Pretreated sample solution introduction step operation
S0033B: Sample introduction step operation
S0034: Washing step operation
S0035: Elution step operation
S005: Measurement at detector
S004: Sample post-treatment operation

The invention claimed is:

1. An analyzer comprising:
a first disk on which a sample container containing a sample and a disposable container can be placed,
a second disk on which a solid-phase extraction cartridge for conducting solid-phase extraction and a disposable container can be placed,
a third disk which is located under the solid-phase extraction cartridge and on which a receiver container for receiving an eluate after the solid-phase extraction can be placed,
a reagent storage part in which a reagent container can be placed,
a detector which measures a solid-phase extracted sample,
a first probe capable of transferring the sample in the sample container or a solution in the disposable container placed on the first disk to the solid-phase extraction cartridge or the disposable container placed on the second disk,
a second probe capable of transferring a reagent in the reagent container to the sample container or the disposable container placed on the first disk and to the solid-phase extraction cartridge or the disposable container placed on the second disk, and
a controller that controls the first disk, the second disk, the third disk, the detector, the first probe, and the second probe, wherein the controller is configured to:
transfer the sample in the sample container placed on the first disk to the disposable container placed on the first disk or on the second disk using the first probe,
pretreat the sample before the solid-phase extraction on the first disk using the disposable container placed on the first disk, wherein the pretreatment includes concentrating the sample through liquid-liquid extraction or antigen-antibody reaction, transfer a solution after the sample pretreatment in the disposable container on the first disk to the solid-phase extraction cartridge on the second disk using the first probe, conduct the solid-phase extraction in the solid-phase extraction cartridge on the second disk, elute the eluate after the solid-phase extraction into the receiver container on the third disk measure the solid-phase extracted sample in the receiver container using the detector, and conduct sample post-treatment after the solid-phase extraction including using the disposable container placed on the second disk and wherein in the conducting of sample post-treatment after the solid-phase extraction, the reagent in the reagent container is transferred to the disposable container placed on the first disk or on the second disk using the second probe.

2. An analysis method using an analyzer, wherein the analyzer has a first disk on which a sample container containing a sample and a disposable container can be placed, a second disk on which a solid-phase extraction cartridge for conducting solid-phase extraction and a disposable container can be placed, a third disk which is located under the solid-phase extraction cartridge and on which a receiver container for receiving an eluate after the solid-phase extraction can be placed, a reagent storage part in which a reagent container can be placed, a detector which measures a solid-phase extracted sample, a first probe capable of transferring the sample in the sample container or a solution in the disposable container placed on the first disk to the solid-phase extraction cartridge or the disposable container placed on the second disk and a second probe capable of transferring a reagent in the reagent container to the sample container or the disposable container placed on the first disk and to the solid-phase extraction cartridge or the disposable container placed on the second disk, and wherein the analysis method comprises:

a step of transferring the sample in the sample container placed on the first disk to the disposable container placed on the first disk or on the second disk using the first probe, a step of pretreating the sample before the solid-phase extraction on the first disk using the disposable container placed on the first disk, wherein the step of pretreating the sample includes concentrating the sample through liquid-liquid extraction or antigen-antibody reaction, a step of transferring a solution after the sample pretreatment in the disposable container on the first disk to the solid-phase extraction cartridge on the second disk using the first probe, a step of conducting the solid-phase extraction in the solid-phase extraction cartridge on the second disk, a step of eluting the eluate after the solid-phase extraction into the receiver container on the third disk a step of measuring the solid-phase extracted sample in the receiver container using the detector and a step of conducting sample post-treatment after the solid-phase extraction includes using the disposable container placed on the second disk and wherein in the step of conducting sample post-treatment after the solid-phase extraction, the reagent in the reagent container is transferred to the disposable container placed on the first disk or on the second disk using the second probe.

3. The analysis method according to claim 2 wherein a plurality of samples are measured and the measurement of a sample which is subjected to the sample pretreatment is started prior to the measurement of a sample which is not subjected to the sample pretreatment.

4. The analysis method according to claim 2 wherein the reagent is a derivatization reagent.

* * * * *